United States Patent
Vaughan et al.

(10) Patent No.: US 6,531,544 B1
(45) Date of Patent: Mar. 11, 2003

(54) BLOCK COPOLYMER BASED HOT MELT ADHESIVE FOR BONDING LOTION COATED SUBSTRATES

(75) Inventors: Steve R. Vaughan, St. Paul, MN (US); Greg J. Van Lith, Stillwater, MN (US); Larry S. Flanagan, Vadnais Heights, MN (US)

(73) Assignee: H.B. Fuller Licensing & Financing, Inc., St. Paul, MN (US)

( * ) Notice: Subject to any disclaimer, the term of this patent is extended or adjusted under 35 U.S.C. 154(b) by 0 days.

(21) Appl. No.: 09/497,296

(22) Filed: Feb. 3, 2000

(51) Int. Cl.[7] .............................................. C08L 53/00
(52) U.S. Cl. ........................ 525/89; 524/270; 524/271; 523/105; 523/111
(58) Field of Search ................................ 524/270, 271, 524/274, 474, 476, 484, 499; 525/88, 89, 90

(56) References Cited

U.S. PATENT DOCUMENTS 5,948,709 A  9/1999 Paul et al.
6,184,285 B1 * 2/2001 Hatfield et al. ............. 524/505

FOREIGN PATENT DOCUMENTS

| EP | 0 802 251 | 10/1997 |
| EP | 1 020 195 | 7/2000 |
| WO | 96 11236 | 4/1996 |
| WO | WO 97/38739 | 10/1997 |
| WO | WO 97/39075 | 10/1997 |
| WO | WO 98/24391 | 6/1998 |
| WO | 99 28405 | 6/1999 |
| WO | WO 99/56796 | 11/1999 |
| WO | 00 17285 | 3/2000 |

* cited by examiner

Primary Examiner—Edward J. Cain
Assistant Examiner—Katarzyna W. Lee

(57) ABSTRACT

The present invention relates to using certain block copolymer based hot melt adhesive compositions for the assembly of disposable absorbent articles such as disposable diapers wherein the adhesive is in contact with an oil-based skin care ingredient, and the resulting disposable absorbent article. The adhesive is particularly useful for adhesively bonding elastic to nonwoven, and exhibits good stress resistance in the presence of lotion.

20 Claims, No Drawings

BLOCK COPOLYMER BASED HOT MELT ADHESIVE FOR BONDING LOTION COATED SUBSTRATES

FIELD OF THE INVENTION

The present invention relates to using certain block copolymer based hot melt adhesive compositions for the assembly of disposable absorbent articles such as disposable diapers wherein the adhesive is in contact with an oil-based skin care ingredient, and the resulting disposable absorbent article. The adhesive is particularly useful for adhesively bonding elastic to nonwoven, and exhibits good stress resistance in the presence of lotion.

BACKGROUND OF THE INVENTION

Hot melt pressure sensitive adhesives based on styrene-isoprene-styrene and/or styrene-butadiene-styrene, tackifying resin(s) and relatively high concentrations of plasticizing oil have been used extensively for the construction of disposable diapers. Block copolymer based adhesives are generally preferred, particularly for elastic attachment, due to the ability of such adhesive compositions to resist creep.

A recent trend in the disposable absorbent product industry has been to introduce certain oil-based skin care ingredients such as baby oil, lotions, ointments, petroleum jellies, sunscreens, etc. into such absorbent products. Typically, such ingredients are coated onto the topsheet that contacts the skin during use of the absorbent products. This trend has made it increasingly difficult to maintain adequate bond strengths in disposable absorbent products throughout the entire product life-cycle, particularly for elastic attachment bonds.

WO 97/39075, published Oct. 23, 1997, teaches an oil resistant polybutylene based hot melt adhesive having a variety of end uses, particularly in the construction and elastic attachment application of nonwoven disposable articles. The composition includes polybutylene copolymer or a mixture of polybutylene and polyolefin polymers, a tackifier resin, plasticizer, a wax, and a stabilizer. According to this reference, hot melt adhesives based on styrene-isoprene-styrene or styrene-butadiene-styrene lose most of their bond strengths upon exposure to mineral oil or other oil based ointments.

Likewise, WO 97/38739 published Oct. 23, 1997 discloses an adhesive that exhibits desired oil-resistance and processing properties. The adhesive is claimed to have a certain elastic modulus and viscosity. An adhesive material comprising styrene-isoprene-styrene rubber block copolymer, hydrocarbon tackifying resins, and mineral oil, is depicted as having a loss of peel from 693 to 196 grams, and a 72% loss of energy upon oil insult.

U.S. Pat. No. 5,948,709 issued to Paul et al. Sep. 7, 1999 is directed to oil resistant compositions and nonwoven articles comprising an adhesive prepared from polymeric dimer fatty acid polyamide resins which are especially suited for use in the elastic attachment of disposable nonwoven products and particularly for leg or waist bond closures for disposable products such as diapers. This reference also states that "block copolymer based adhesives lose most of their bond strength, resulting in adhesive bond failure upon exposure to mineral oil or other oil based ointments which are often used on infants to treat skin rashes. As a result, the elastic leg bands may actually come loose from the diaper resulting in a break down of the inner leg cuff."

SUMMARY OF THE INVENTION

Surprisingly, the present inventors have found that certain block copolymer based hot melt adhesive compositions maintain their bond strength upon exposure to oil-based skin care ingredients such as lotion.

The adhesive composition comprises from about 10 wt-% to about 45 wt-% of a block copolymer component, from about 50 wt-% to about 80 wt-% of at least one tackifying resin, and from 0 to about 10 wt-% of a liquid plasticizer. The Applicants surmise that the low concentration of liquid plasticizer is critical to the ability of the adhesives to maintain adequate bond strength in the presence of oil-based skin care ingredients.

Preferably, the block copolymer component concentration is greater than about 20 wt-% and the tackifying resin concentration ranges from 70 wt-% to 80 wt-%. More preferably, the block copolymer component is a blend of a first, relatively soft lock copolymer and a second, relatively hard block copolymer. The first block copolymer is typically one or more styrene-isoprene-styrene (SIS) block copolymers having a diblock content of at least about 20 wt-%. The second block copolymer is preferably a styrene-butadiene-styrene (SBS) block copolymer having a melt flow rate of less than 10 g/10 minutes. For reduced viscosity and improved processability, one or more of the block copolymers are preferably radial.

The adhesive is useful for bonding a variety of substrates that contain or are coated with oil-based ingredients. The adhesive is particularly useful in the assembly of disposable absorbent articles for adhesively bonding nonwoven, film, and particularly elastic and elastomeric films and substrates.

In one embodiment, the present invention is a disposable article having at least one substrate bonded with a hot melt adhesive wherein said adhesive comprises:

(a) from about 15 wt-% to about 45 wt-% of a block copolymer component;

(b) from about 50 wt-% to about 80 wt-% of at least one tackifying resin; and (c) from 0 to about 10 wt-% of an oil plasticizer;

wherein said adhesive is in contact with an oil-based skin care ingredient.

In another embodiment, the present invention is a method of using a hot melt adhesive composition in the assembly of disposable absorbent articles comprising the steps of:

(a) providing a molten hot melt adhesive composition comprising:
  (i) from about 15 wt-% to about 45 wt-% of block copolymer component;
  (ii) from about 50 wt-% to about 80 wt-% of at least one tackifying resin; and
  (iii) from 0 to about 10 wt-% of an oil plasticizer;

(b) applying said adhesive to a substrate wherein said adhesive contacts an oil-based skin care ingredient.

DETAILED DESCRIPTION OF THE INVENTION

The adhesive composition contains a block copolymer component that contains one or more block copolymers in an amount ranging from about 10 wt-% to about 45 wt-%, preferably from about 15 wt-% to about 30 wt-% and most preferably from about 20 wt-% to about 30 wt-%.

A wide variety of block copolymers are useful in the present invention including A-B-A triblock structures, A-B diblock structures, $(A-B)_n$ radial block copolymer structures, as well as branched and grafted versions of such, wherein the A endblock is a non-elastomeric polymer block, typically comprising polystyrene, and the B block is an unsaturated conjugated diene or hydrogenated version thereof. In general, the B block is typically isoprene, butadiene, ethylene/butylene (hydrogenated butadiene), ethylene/propylene (hydrogenated isoprene), and mixtures thereof. The block copolymers comprising an unsaturated conjugated diene such as styrene-isoprene-styrene (SIS), styrene-butadiene-styrene (SBS) and mixtures thereof are preferred due to their increased tack and reduced cost. Commercial embodiments include the Kraton® D series block copolymers, available from Shell Chemical Company (Houston, Tex.), Europrene® Sol T block copolymers available from EniChem (Houston, Tex.), Vector® block copolymers available from Exxon (Dexco) (Houston, Tex.), Solprene® block copolymers from Housmex® (Houston, Tex.) as well as others.

In addition to the block configuration, block copolymers are typically characterized according to their reported styrene content, diblock content, and in terms of their melt flow rate (MFR, Condition G) or solution viscosity, which relates to the molecular weight of the block copolymer.

Typically, the non-elastomeric A block (styrene) concentration ranges from about 5 wt-% to about 45 wt-% with respect to the total weight of the block copolymer. The styrene portion is less susceptible to heat degradation. Accordingly, hot melt adhesive compositions based on higher styrene content block copolymers generally exhibit enhanced heat stability relative to hot melt adhesive compositions based on block copolymer having a lower styrene content. However, high styrene content (>30%) are typically not available in low melt flow rate grades. Since employing at least one block copolymer having a low melt flow rate is surmised to be critical to the invention, the styrene content of the preferred block copolymers typically ranges from about 15 wt-% to about 30 wt-% with respect to the total weight of the block copolymer.

In general, block copolymers range in AB diblock content from 0, wherein the block copolymer is 100% coupled, as in the case of several grades of the Vector® block copolymers, to 100% diblock, as in the case of multi-arm $(EP)n^8$ block copolymers. For increased tack and improved adhesion, preferably one or more of the block copolymers employed in the adhesive of the invention contain diblock. More preferably, the diblock content of such block copolymers ranges from about 20 wt-% to about 50 wt-%.

The molecular weight of a block copolymer is related to its melt flow rate (MFR) and its solution viscosity at 77° F. for a given weight of polymer in toluene. Generally, a MFR is reported for grades of block copolymers that are sufficiently low enough in molecular weight such that the MFR can be measured according to Condition G (ASTM-1238, 200° C./5 kg). For block copolymers in which the molecular weight is too high to measure the MFR, a solution viscosity is typically reported by the supplier. The amount of block copolymer employed for determining the solution viscosity varies depending on the molecular weight. For the high molecular weight block copolymers, the solution viscosity may be expressed as a function of a 10 wt-% or 15 wt-% block copolymer solution, whereas for more conventional and moderate molecular weight block copolymers, a 25 wt-% block copolymer solution is employed. The adhesive of the present invention preferably employs at least one block copolymer having a melt flow rate of less than about 20 g/10 min. and more preferably about 15 g/10 min or less.

The adhesive composition for use in the invention, preferably comprises a blend of block copolymer wherein the first block copolymer is relatively soft, or low in modulus, in comparison to the second block copolymer. According the first (soft) block copolymer typically differs from the second block copolymer with regard to the selection of midblock, the structure of the block copolymer, the styrene content, and the diblock content.

The first block copolymer is typically an SIS block copolymer having a styrene content of about 30 wt-% or less, more preferably about 20 wt-%, and most preferably about 15% styrene or less, relative to the total weight of the block copolymer. The first block copolymer may be 100% triblock and thus not contain any appreciable diblock. Preferably however, the first block copolymer contains a diblock in amount greater than 20 wt-% of the total weight of the block copolymer and more preferably about 30 wt-% diblock or greater. In a preferred embodiment, the soft block copolymer component is a blend of a linear SIS block copolymer and a radial SIS block copolymer, each having a diblock content of at least 20 wt-%.

The second block copolymer may also be SIS, but is preferably SBS and most preferably radial SBS. The second (hard) block copolymer typically has a styrene content of about 30 wt-% or greater. In the case of block copolymer having a styrene content of greater than 40 wt-% the melt flow rate is typically relatively high, about 30 MFR or greater. Preferably, the second block copolymer has a styrene content of about 30 wt-% or lower and a melt flow rate of less than 10 g/10 min. More preferably the second block copolymer is sufficiently high in molecular weight such that the solution viscosity, rather than the melt flow rate is reported. In a preferred embodiment the solution viscosity of the second block copolymer is greater than 5,000 cps for a 25 wt-% solution of polymer and toluene at 20° C., preferably greater than about 10,000 cps, more preferably greater than about 15,000, and most preferably about 20,000 cps or greater.

The hot melt adhesive composition of the invention comprises at least one tackifier. As used herein, the term "tackifier" or "tackifying resin" means any of the compositions described below that are useful to shift the Tg (glass transition temperature) of the polymer to a higher temperature and impart tack to the hot melt adhesive composition. ASTM D-1878-61T defines tack as "the property of a material which enables it to form a bond of measurable strength immediately on contact with another surface". Typically the amount of tackifying resin ranges from about 40 wt-% to about 80 wt-% of the total weight of the adhesive. In order to minimize the plasticizing oil concentration, the adhesive composition preferably comprises at least about 50 wt-%, more preferably at least about 60 wt-%, and most preferably about 70 wt-% tackifying resin.

In general terms, the tackifying resins useful in the adhesives of the invention comprise resins derived from renewable resources such as rosin derivatives including wood rosin, tall oil, gum rosin as well as rosin esters and natural and synthetic terpenes, and derivatives of such. Aliphatic, aromatic or mixed aliphatic-aromatic petroleum based tackifiers are also useful in the adhesives of this invention. Representative examples of useful hydrocarbon resins includes alpha-methyl styrene resins, branched and unbranched $C_5$ resins, $C_9$ resins, dicyclopentadiene (DCPD) based resins, as well as styrenic and hydrogenated modifications of such. Tackifying resins range from being a liquid at about 25° C. (room temperature) to having a ring and ball softening point up to about 150° C. The tackifier or tackifier mixture preferably has a softening point of greater than about 80° C., more preferably about 100° C. or higher.

Preferably, a predominant amount of the tackifier is what is commonly known as a mid-block tackifying resin. In the case of block copolymers having unsaturated midblocks such as isoprene, the preferred tackifying resin is a hydrogenated DCPD or C9 resin; whereas for block copolymers having unsaturated butadiene midblocks, rosin derivatives such as rosin esters and hydrogenated styrenated terpene resins are preferred.

The adhesive composition of the present invention may optionally comprise a plasticizing liquid in an amount up to about 10 wt-%. In the context of the present invention a plasticizing liquid is defined as a flowable diluent having a molecular weight (Mw) of less than 3000, preferably less than 2000, and more preferably less than 1000. A small amount of plasticizing oil is preferred to soften the adhesive, improving its elasticity and extensibility. Block copolymer compositions having higher concentrations of plasticizing oil have been found to exhibit diminished bond strength when employed to bond lotion coated substrates, consistent with the teaching of the previously cited art references. The Applicants surmise that the hot melt adhesive composition of the present invention is not resistant to oil-based skin care products such as lotions in the traditional sense, wherein the composition does not absorb or become plasticized by oil. Rather, the compositions are believed to be "robust" with respect to oil absorption, meaning that the composition is surmised to absorb oil to some extent, yet the absorption of oil does not detrimentally affect the adhesive properties.

Plasticizing oils are primarily hydrocarbon oils which are low in aromatic content and which are paraffinic or naphthenic in character. Plasticizing oils are preferably low in volatility, transparent and have as little color and odor as possible. The use of plasticizing liquids in the invention also contemplates the use of liquid resins, olefin oligomers, liquid elastomer, low molecular weight polymers, vegetable oils and other natural oils as well as similar plasticizing liquids.

In the case of construction adhesives, solid plasticizers such as cyclohexane dimethanol dibenzoate and phthalate esters, may optionally be employed at amounts ranging up to about 40 wt-% and preferably at amount ranging from about 10 wt-% to about 20 wt-%. However, in the case of elastic attachment adhesives, solid plasticizers tend to be avoided, since their presence reduces the rate of set. In the absence of a fast rate of set, elastomeric substrate that have been extended have the opportunity to relax prior to solidification of the adhesive. Further, as is known in the art, various other components can be added to modify the tack, color, odor, etc., of a hot melt adhesive. Additives such as antioxidants (for example, hindered phenolics (for example, Irganox® 1010, Irganox® 1076), phosphates (for example, Irgafos® 168), antiblock additives, pigments, and fillers, can also be included in the formulations.

The finished adhesive is typically light in color, having a molten Gardner color of less than about 6 and preferably less than about 4. Preferably the viscosity is less than 30,000 cPs at 350° F. and more preferably ranges from about 3,000 to about 15,000 cPs. Particularly for elastic attachment, the adhesive preferably has a ring and ball softening point of at least 190° F. and preferably greater than 200° F.

The amount of acceptable creep is dependent to some extent on the test method employed. In the case of relatively severe test conditions as employed in the examples of the present invention, the creep is preferably less than about 40%, and more preferably less than about 25% for at least about 8 hours at body temperature.

Broadly, disposable absorbent articles such as disposable diapers, feminine protection articles, incontinent pads, bed pads, surgical drapes and gowns, and similar articles are intended for absorption of and shielding from body fluids. Such articles are typically made by (adhesively) bonding one or more substrate layers. The various materials that are suitable for manufacturing such disposable absorbent articles, methods of manufacturing, as well as various product designs, etc. are known from a multitude of patents, such as U.S. Pat. No. 5,957,906 issued to Roe et al. Sep. 28, 1999, incorporated herein by reference. The present invention is not limited to any particular combination of substrates or product design, but rather is useful for bonding substrates that are coated with an oil-based skin care ingredient either prior to or after bonding. Further, the adhesive is also surmised to be useful for bonding highly plasticized substrates such as films or nonwovens based on elastomeric polymers that are blended with oil.

In general, the exterior of a disposable absorbent article, also known as the "backsheet", is typically a body fluid impermeable barrier layer. Such barriers are usually provided as a film roll good and comprised of polyolefin materials such as polyethylene or ethylenic copolymers such as ethylene-vinyl acetate. Alternatively, the barrier layer can be made by coating a thermoplastic composition onto a carrier material, such as a nonwoven. In this instance, the exterior of the article is often nonwoven rather than a plastic film. The barrier layer is typically bonded to one or more absorbent layers comprised of cellulosic pulp or fluff, superabsorbent batts, and combinations of such absorbent materials. Fluff layers are often formed and wrapped in tissue to provide mechanical integrity to the fluff. The absorbent layer is sandwiched between the fluid impervious backsheet and a body fluid pervious cover or "topsheet". Such covers are typically nonwovens or aperatured films. The backsheet is typically joined to the topsheet, the absorbent core or any other element of the diaper by a what is commonly called a "construction adhesive." The construction adhesive may be applied by a continuous layer of adhesive, a patterned layer of adhesive, or an array of separate lines, spirals, or spots of adhesive.

Various elastic filaments, threads or ribbons are often bonded between the backsheet and topsheet at the periphery of disposable diapers, and some feminine protection articles to improve the fit to the body and improve containment. Elastic materials are also incorporated into the topsheet layer to form "leg cuffs", that provide improved containment of liquids and other body exudates. Leg cuffs may also be referred to as leg bands, side flaps, barrier cuffs, or elastic cuffs. (See U.S. Pat. Nos. 3,860,003; 4,808,178; 4,909,803; 4,695,278 and 4,795,454 incorporated herein by reference. Elastomeric substrates such as extensible films, nonwovens, and laminates may also be incorporated as alternative leg cuff, waist band or leg attachment features as well as for side panels. In the context of the present invention, "elastic attachments" refers to the adhesive bonding of any of such substrates in which the adhesive is required to resist relaxation to a stress that is induced by the extension of an elastomeric material or substrate. In general, the bonding of elastic materials is typically more difficult, employing an "elastic attachment adhesive". In some instances both construction and elastic attachment employ the same "multipurpose" adhesive. Elastic attachment is commonly achieved by applying adhesive to the elastic. The adhesive can be extruded or applied in a spray, spiral, or intermittent pattern. Preferably, the adhesive is applied according to the teachings of U.S. Pat. No. 4,842,666 issued to Werenicz on Jun. 27, 1989, incorporated herein by reference, wherein the adhesive is sprayed such that it form a web-like adhesive pattern about the elastic. Other preferred methods for applying the adhesive include the Omega™ application equipment available from ITW as well as Nordon's Duraweave™ application equipment.

Any substrate and typically the topsheet may be coated with a lotion as is known in the art. Examples of suitable lotions including those described in U.S. Pat. No. 5,607,760 entitled "Disposable Absorbent Article Having A Lotioned Topsheet Containing an Emollient and a Polyol Polyester Immobilizing Agent" issued to Roe on Mar. 4, 1997; U.S. Pat. No. 5,609,587 entitled "Diaper Having A Lotion Topsheet Comprising A Liquid Polyol Polyester Emollient And An Immobilizing Agent" issued to Roe on Mar. 11, 1997; U.S. Pat. No. 5,635,191 entitled "Diaper Having A Lotioned Topsheet Containing A Polysiloxane Emollient" issued to Roe et al. on Jun. 3, 1997; U.S. Pat. No. 5,643,588 entitled "Diaper Having A Lotioned Topsheet" issued to Roe et al. on Jul. 1, 1997; and WO 98/24391 published Jun. 11, 1998 entitled "Absorbent Article Having Lotioned Leg Cuffs".

The invention is further exemplified by the following non-limiting examples.

EXAMPLES

Test Methods

1. Brookfield Viscosity was measured with a RVDT model viscometer in accordance with the manufacturer's operating instructions.
2. Creep Resistance is used to evaluate an adhesive's ability to withstand the stress imparted on the adhesive-elastic bond when held in an elongated state at the use temperature of the disposable article.

Elastic attachment lamination test samples are prepared by adhering 3 strands of Spandex (940 available from Decitex) between polyethylene film (HTS-5 available from Tredegar) and nonwoven (0.68 oz spunbond available from Fiberweb) according to the previously cited Werenicz et al. method. The following application conditions were employed.

Web Speed—350 ft/min.
Adhesive Temperature—350° F. (177° C.)
Air Temperature—50° F. higher than the adhesive temperature
Nip Pressure—30 psi
Coat Weight—0.020 g/in²
Elastic Elongation—300%

In finished disposable diapers, the elastic is extended the entire length of the diaper during manufacturing, yet only adhesively attached in the mid-portion that forms the leg opening. Once the individual diapers are cut and separated from each other, the unadhered elastic returns to its unelongated state forming an end-point for testing the creep resistance. However, when making elastic laminates for testing purposes as described above, the elastic bond is continuous, lacking end-points. Thus, end points are artificially created. Specifically, 12" portions of the polyethylene-elastic-nonwoven laminate are anchored to a piece of cardboard at 95% of full extension. The individual strands of elastic are cut at each end of the attachment such that the strand is able to move within the lamination. The samples are then place in a 100° F. oven for 8 hours, marking the amount of elastic retraction (creep) at 1, 4 and 8 hours.

In comparative testing, this method has been shown to be more severe than testing on finished disposable diapers.

Comparative Example A

| PPH | Tradename | Chemical Description |
|---|---|---|
| 20 | Vector ® 4211 | 29% styrene, 100% coupled, 13 MFR Linear SIS Block Copolymer (Exxon) |
| 55.6 | Escorez ® 5400 | Hydrogenated Dicyclopentadiene Tackifying Resin (Exxon) |
| 9 | Endex ® 160 | 160° Softening Point Alpha-Methyl Styrene Endblock Tackifying Resin (Hercules) |
| 15 | | 500 SUS naphthenic oil |
| 0.4 | Irganox ® 1010 | Hindred Phenol Antioxidant (Ciba Giegy) |

Example 1

| PPH | Tradename | Chemical Description |
|---|---|---|
| 10 | Vector ® 4114 | 15% styrene, 42% diblock, 25 MFR Linear SIS Block Copolymer (Exxon) |
| 8 | Solprene ® 411 | 30% styrene, <0.5 MFR (190° C./5 kg) 19 Pa.s for25% at 20 C Radial SBS Block Copolymer (Negromex) |
| 5.0 | Kraton ® D1124P | 30% styrene, 30% diblock, 4 MFR Radial SIS Block Copolymer (Shell) |
| 64.0 | Sylvares ® ZT 105 | hydrogenated styrenated terpene tackifying resin |
| 5.0 | Hercolite ® 290 | Alpha-Methyl Styrene Endblock Reinforcing Tackifying Resin |
| 7 | | 500 SUS naphthenic oil |
| 0.4 | Irganox ® 1010 | Hindred Phenol Antioxidant |

Brookfield Viscosity
@ 300° F.  36,400
@ 325° F.  18,900
@ 350° F.  11,000
@ 375° F.  6,900

Example 2

| PPH | Tradename | Chemical Description |
|---|---|---|
| 15 | Vector ® 4211 | 29% styrene, 100% coupled, 13 MFR Linear SIS Block Copolymer |
| 10 | Vector ® 4411 | 44% styrene, 100% coupled, 40 MFR Linear SIS Block Copolymer |
| 63.7 | Escorec ® 5400 | Hydrogenated Dicyclopentadiene Tackifying Resin |
| 10 | Endex ® 160 | 160° Softening Point Alpha-Methyl Styrene Endblock Tackifying Resin |
| 0.4 | Irganox ® 1010 | Hindred Phenol Antioxidant |

Brookfield Viscosity
@ 275° F.  99,000
@ 399° F.  32,050
@ 325° F.  6,400

Example 1 was employed to make elastic attachment bonds as described in the "Creep Resistance" test method. In order to determine the effect of the lotion on the adhesive, a "Control" sample was prepared. A "Lotion" sample was prepared in which one of the nonwoven substrates was coated with 0.008 gsm of lotion, per the teachings of WO 98/24391 published Jun. 11, 1998, incorporated herein by reference. The "Creep Resistance" was tested, reporting the average creep of 15 strands of spandex with the standard deviation in parentheses:

|         | Control | Lotion |
| ------- | ------- | ------ |
| 1 hour  | 4(1)    | 8(1)   |
| 4 hours | 7(1)    | 16(3)  |
| 8 hours | 9(1)    | 19(3)  |

Elastic attachment bonds were prepared with Example 2 and Comparative A in a similar manner. Example 2 was also found to have suitable creep resistance, yet not as good of adhesion properties as Example 1, particularly for elastic attachment. Comparative A, on the other hand, exhibited good creep resistance when employed with uncoated substrated. However, when employed to bond lotion coated nonwoven, the creep at 4 hours was unacceptably high at about 50%

What is claimed is:

1. A disposable article comprising:
   a) a composition comprising oil;
   b) at least one substrate; and
   c) a hot melt adhesive bonded to the substrate and in contact with said oil of said composition,
   the hot melt adhesive comprising
      i) from about 15% by weight to about 45% by weight block copolymer,
      ii) from about 50% by weight to about 80% by weight tackifying resin, and
      iii) from 0% by weight to 10% by weight liquid plasticizer.

2. The disposable article of claim 1 wherein the block copolymer component comprises a blend of at least one first block copolymer and at least one second block copolymer.

3. The disposable article of claim 2 wherein the first block copolymer has a diblock content of at least 20 wt-% with respect to the total weight of the block copolymer.

4. The disposable article of claim 2 wherein the first block copolymer is a styrene-isoprene-styrene block copolymer.

5. The disposable article of claim 2 wherein the second block copolymer has a melt flow rate of less than about 20 g/10 minutes.

6. The disposable article of claim 2 wherein the second block copolymer has a melt flow rate of less than about 10 g/10 minutes.

7. The disposable article of claim 2 wherein the second block copolymer is styrene-butadiene-styrene.

8. The disposable article of claim 2 wherein at least one of said block copolymers is radial.

9. The disposable article of claim 1 wherein the amount of tackifying resin of the adhesive ages from about 60 wt-% to about 80 wt-%.

10. The disposable article of claim 1 wherein the amount of tackifying resin of the adhesive ranges from about 70 wt-% to about 80 wt-%.

11. The disposable article of claim 1 wherein the liquid plasticizer is an oil.

12. The disposable article of claim 1 wherein the substrate is elastic.

13. The disposable article of claim 1 wherein the substrate is nonwoven.

14. The disposable article of claim 1 wherein the substrate is a film.

15. The disposable article of claim 1 wherein said adhesive has a viscosity of less than about 30,000 cps at 350° F.

16. The disposable article of claim 1 wherein said tackifying resin of said adhesive has a ring and ball softening temperature of at least 100° C.

17. A method of using a hot melt adhesive, said method comprising:
    applying a molten hot melt adhesive composition to a substrate comprising oil, said hot melt adhesive composition comprising
       i) from about 15% by weight to about 45% by weight block copolymer,
       ii) from about 50% by weight to about 80% by weight tackifying resin, and
       iii) from 0% by weight to 10% by weight liquid plasticizer,
    said applied adhesive being in contact with said oil of said substrate and forming an adhesive bond to said substrate.

18. The method of claim 17 wherein said substrate is elastic.

19. The method of claim 18 further comprising the step of contacting said adhesive coated elastic to nonwoven forming a laminate.

20. The method of claim 19 wherein said laminate has a creep of less than about 25%.

* * * * *

UNITED STATES PATENT AND TRADEMARK OFFICE
CERTIFICATE OF CORRECTION

PATENT NO. : 6,531,544 B1
DATED : March 11, 2003
INVENTOR(S) : Vaughan et al.

It is certified that error appears in the above-identified patent and that said Letters Patent is hereby corrected as shown below:

Column 5,
Line 51, "phosphates" should be -- phosphites --

Column 10,
Line 6, "ages" should be -- ranges --

Signed and Sealed this

Twelfth Day of August, 2003

JAMES E. ROGAN
*Director of the United States Patent and Trademark Office*